(12) United States Patent
Satyanarayana et al.

(10) Patent No.: US 7,439,387 B2
(45) Date of Patent: Oct. 21, 2008

(54) PROCESS FOR THE PREPARATION OF GABAPENTIN FORM-II

(75) Inventors: Chava Satyanarayana, Secunderabad (IN); Gorantla Seeta Ramanjaneyulu, Secunderabad (IN); Indukuri Venkata Sunil Kumar, Hyderabad (IN)

(73) Assignee: Matrix Laboratories Ltd., Secunderabad (IN)

( * ) Notice: Subject to any disclaimer, the term of this patent is extended or adjusted under 35 U.S.C. 154(b) by 549 days.

(21) Appl. No.: 10/553,821

(22) PCT Filed: Apr. 16, 2004

(86) PCT No.: PCT/IN2004/000102

§ 371 (c)(1),
(2), (4) Date: Oct. 19, 2005

(87) PCT Pub. No.: WO2004/093780

PCT Pub. Date: Nov. 4, 2004

(65) Prior Publication Data

US 2006/0235079 A1    Oct. 19, 2006

(30) Foreign Application Priority Data

Apr. 21, 2003    (IN) .......................... 330/MAS/2003

(51) Int. Cl.
   *C07C 61/08*    (2006.01)
(52) U.S. Cl. ..................................... 562/507
(58) Field of Classification Search .................. None
   See application file for complete search history.

(56) References Cited

U.S. PATENT DOCUMENTS

| | | | |
|---|---|---|---|
| 4,024,175 A | 5/1977 | Satzinger et al. | |
| 4,087,544 A | 5/1978 | Satzinger et al. | |
| 4,894,476 A | 1/1990 | Butler et al. | |
| 5,068,413 A | 11/1991 | Steiner et al. | |
| 5,091,567 A | 2/1992 | Geibel et al. | |
| 5,095,148 A | 3/1992 | Mettler et al. | |
| 5,132,451 A | 7/1992 | Jennings et al. | |
| 6,465,689 B1 | 10/2002 | Bryans et al. | |
| 6,846,950 B2 * | 1/2005 | Ferrari et al. | 562/507 |
| 2003/0009055 A1 | 1/2003 | Velardi et al. | |
| 2004/0034248 A1 * | 2/2004 | Bercovici et al. | 562/507 |
| 2004/0068011 A1 | 4/2004 | Cannata et al. | |

FOREIGN PATENT DOCUMENTS

| | | |
|---|---|---|
| EP | 1174418 | 1/2004 |
| WO | WO 98/28255 A1 | 7/1998 |
| WO | WO 99/14184 A1 | 3/1999 |
| WO | WO 00/01660 A1 | 1/2000 |
| WO | WO 02/34709 A1 | 5/2002 |
| WO | WO 02/44123 A1 | 6/2002 |

* cited by examiner

*Primary Examiner*—Karl J Puttlitz
(74) *Attorney, Agent, or Firm*—Schweitzer Cornman Gross & Bondell LLP

(57) ABSTRACT

The present invention relates to a new industrial feasible process for the preparation of Gabapentin Form-II via a novel intermediate Gabapentin hemisulphate hemihydrate with out forming Gabapentin Form-III by neutralizing the Gabapentin hemisulphate hemihydrate solution with a base at higher temperatures followed by cooling to yield Gabapentin Form II with sulphate ions less than 100 ppm with respect to Gabapentin.

17 Claims, 7 Drawing Sheets

PROCESS FOR THE PREPARATION OF GABAPENTIN FORM-II

The present invention relates to a new industrial feasible process for the preparation of Gabapentin Form-II via a novel intermediate Gabapentin hemisulphate hemihydrate.

Gabapentin (i.e. 1-aminomethyl-1-cyclohexaneacetic acid) of the formula is the active

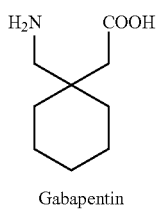

Gabapentin ingredient used for the treatment of various cerebral diseases like epilepsy, hypokinesia including fainting and other brain trauma and in general, it is deemed to produce an improvement in the cerebral functions.

Gabapentin and several processes for its preparation as the Hydrochloride salt, sodium salts are disclosed in U.S. Pat. Nos. 4,024,175 and 4,087,544.

All processes described in the prior art e.g. in US Patent Application No. US 2003/0009055, U.S. Pat. No. 6,465,689, U.S. Pat. No. 5,091,567, PCT publications WO 02/44,123, WO 02/34,709, WO 00/01,660, WO 99/14,184 and European patent EP 1,174,418, yields Gabapentin hydrochloride, which is converted to the corresponding free amino acid by neutralization with a basic ion-exchanger followed by crystallization. U.S. Pat. No. 4,894,476 specifically discloses a method for converting the hydrochloride salt into a crystalline monohydrate by eluting the aqueous solution through a basic ion-exchange resin, producing a slurry from the elute, adding an alcohol to the slurry and isolating by centrifuging followed by drying.

Alternate methods disclosed in U.S. Pat. No. 5,132,451, U.S. Pat. No. 5,095,148, U.S. Pat. No. 5,091,567 and U.S. Pat. No. 5,068,413 involve hydrogenation of the cyano intermediate to liberate the free amino acid.

PCT publication No. WO 98/28255 discloses a method for the conversion of Gabapentin hydrochloride into Gabapentin Form-II via Gabapentin Form-III by elaborate multistep procedure of dissolution into a solvent, filtration of inorganics, distillation of solvent under vacuum in a heating bath at temperature below 35° C., then adding a second solvent, and neutralizing with a base at 25° C. to yield Form-III. Form-III is then converted to Form-II by slurrying in methanol at 25° C. for 14 hrs or recrystallizing it from methanol.

The method of conversion of Gabapentin hydrochloride into Form-II disclosed in PCT Publication WO 98/28255 involves an additional step for the conversion of form-III to required Form-II there by extra loss in the yield. Moreover in the conversion of hydrochloride salt into Gabapentin with substantially very low content of chloride ions requires extensive care and base was required. During the conversion of Gabapentin hydrochloride into free amino acid by the above method the lactam impurity was observed.

In view of all the problems still there is a requirement of an industrial feasible process for preparation of Gabapentin Form-II with substantially lactam free and very low content of chloride ions.

The main object of the present invention is to provide a new industrially feasible process for the preparation of Gabapentin Form-II without the formation of Form-III.

Another object of the invention is to provide a process for the preparation of Gabapentin Form-II free from chloride and lactam impurities.

Yet another object of the invention is to prepare a novel intermediate Gabapentin hemisulphate hemihydrate for its use in the preparation of Gabapentin Form-II.

Yet another object of the invention is to provide fingerprinting of Gabapentin hemisulphate hemihydrate using XRD, IR and chemical analysis.

Reaction of 1,1-cyclohexane diacetic acid monoamide in the presence of alkali hypo halite followed by acidification with sulphuric acid in presence of an organic solvent to extract the liberated sulphate salt into that solvent. An ante solvent is added to crystallize the Gabapentin sulphate salt. The separated salt is then, suspending in organic solvent and neutralizing with a base at a specified temperature range, cooled to ambient temperature, followed by separation of Gabapentin Form-II, which is further purified by slurrying in ethanol.

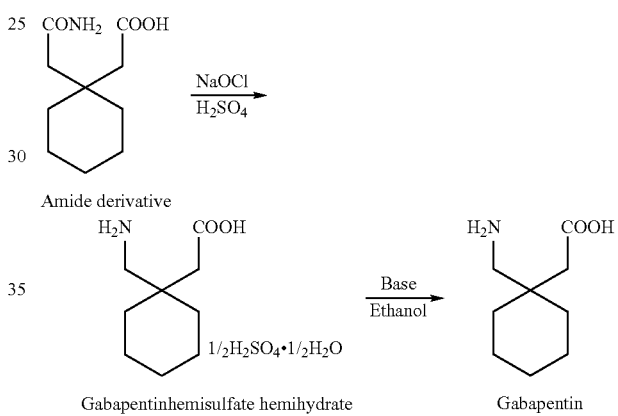

TABLE 1

Figure 1:
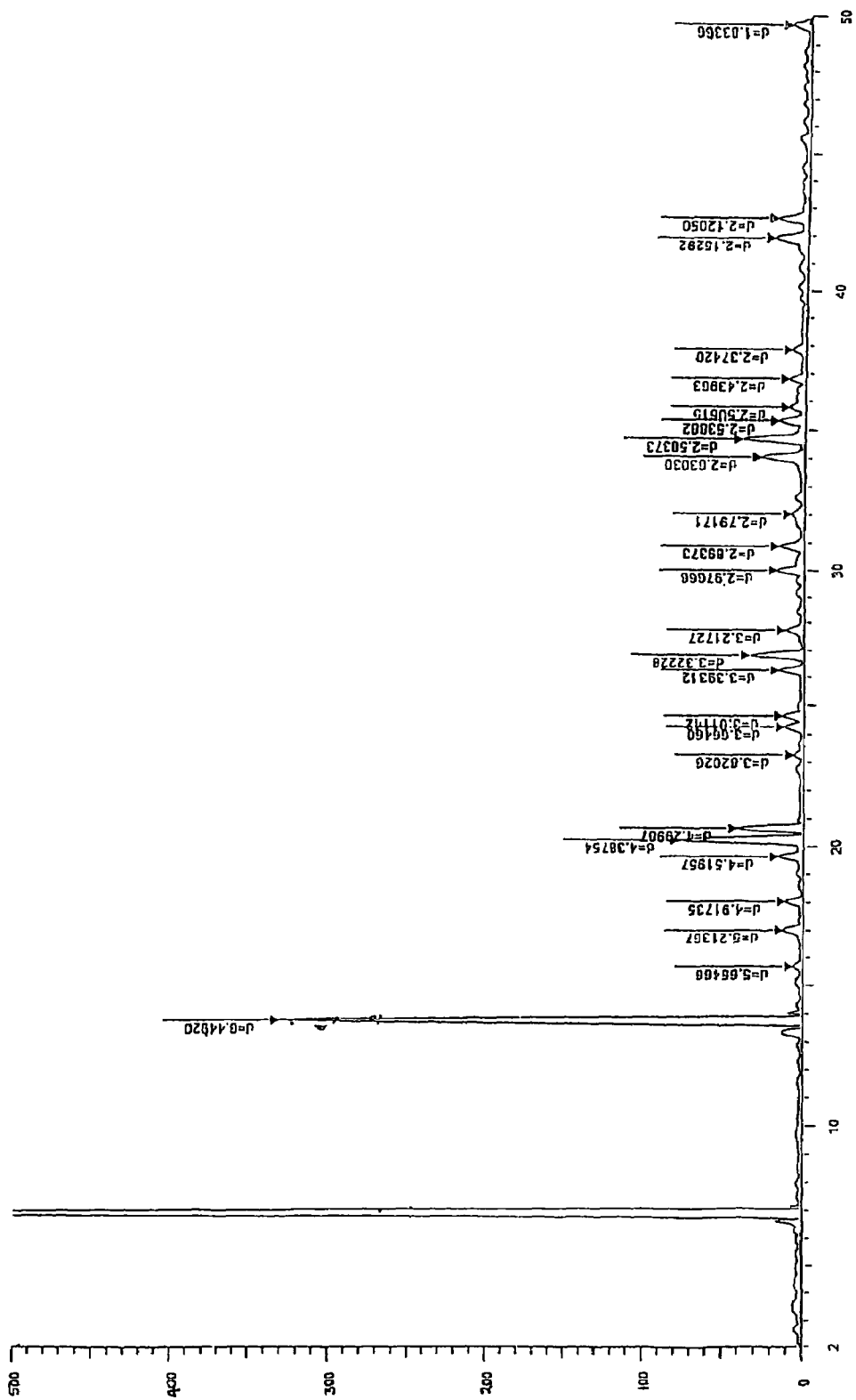
FIG. 1 is the X-ray diffraction pattern of the Gabapentin hemisulphate hemihydrate
Figure 2:
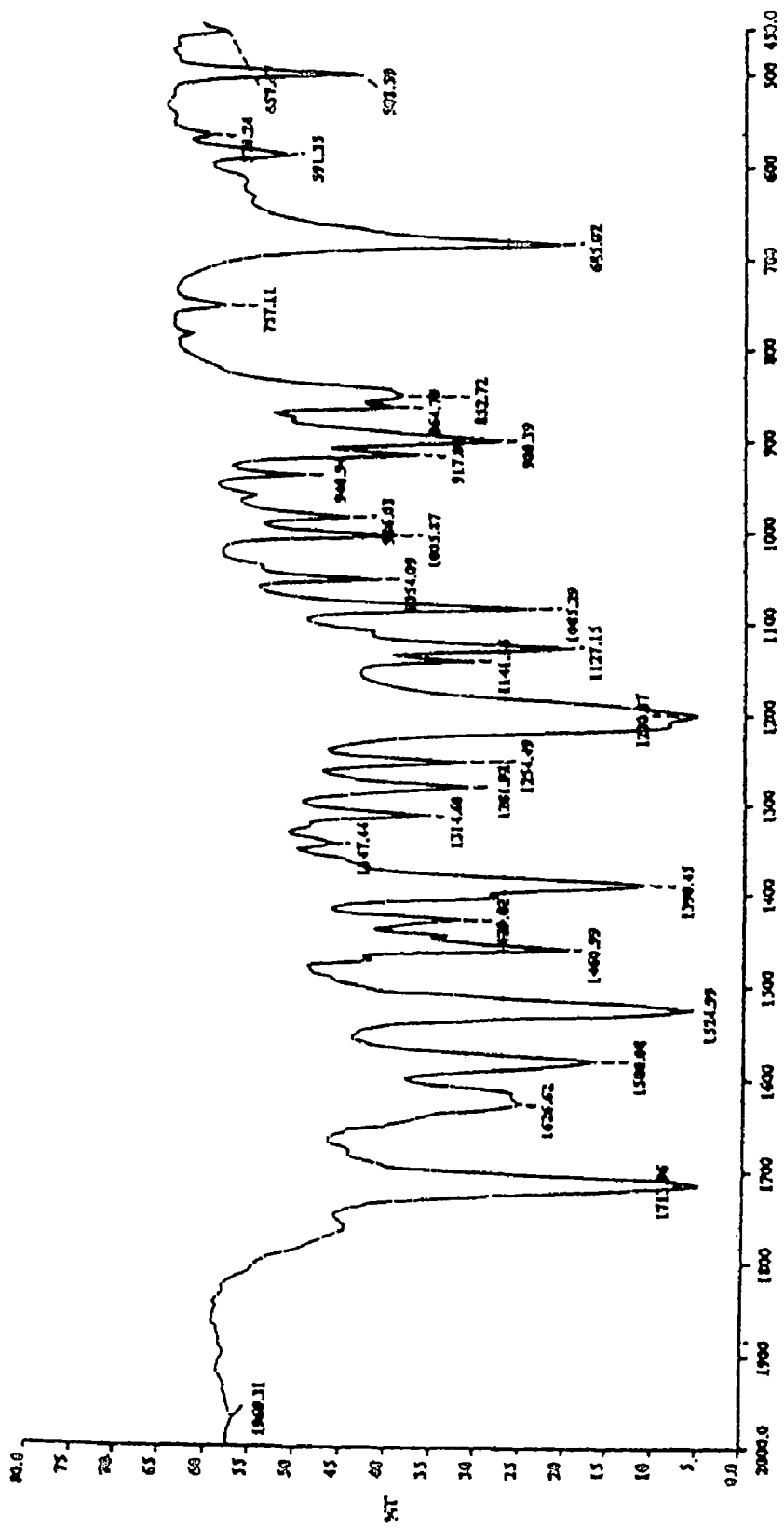
FIG. 2 is the FTIR spectrum of the Gabapentin hemisulphate hemihydrate
Figure 3:
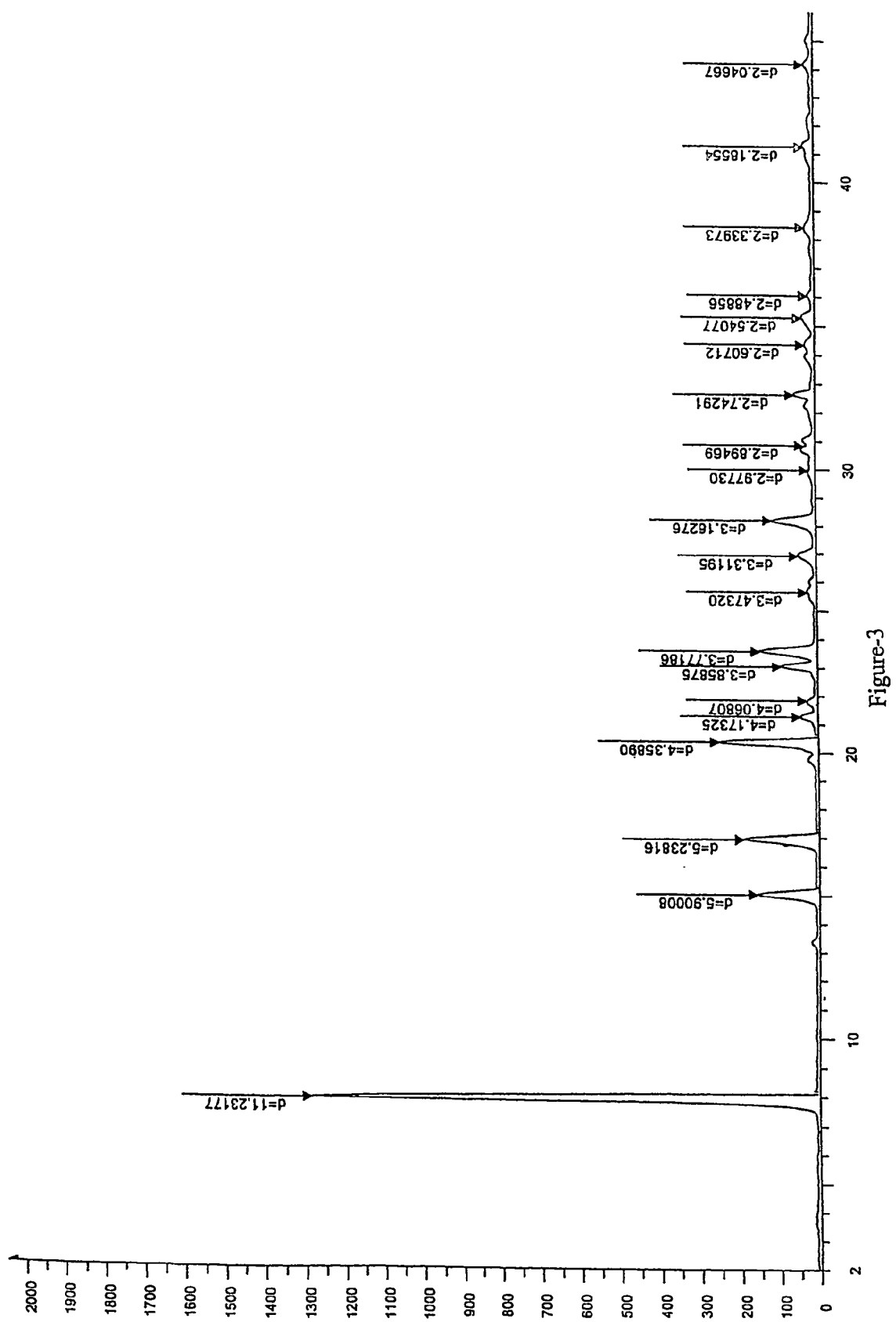
FIG. 3 is the X-ray diffraction pattern of the Gabapentin Form-II
Figure 4:
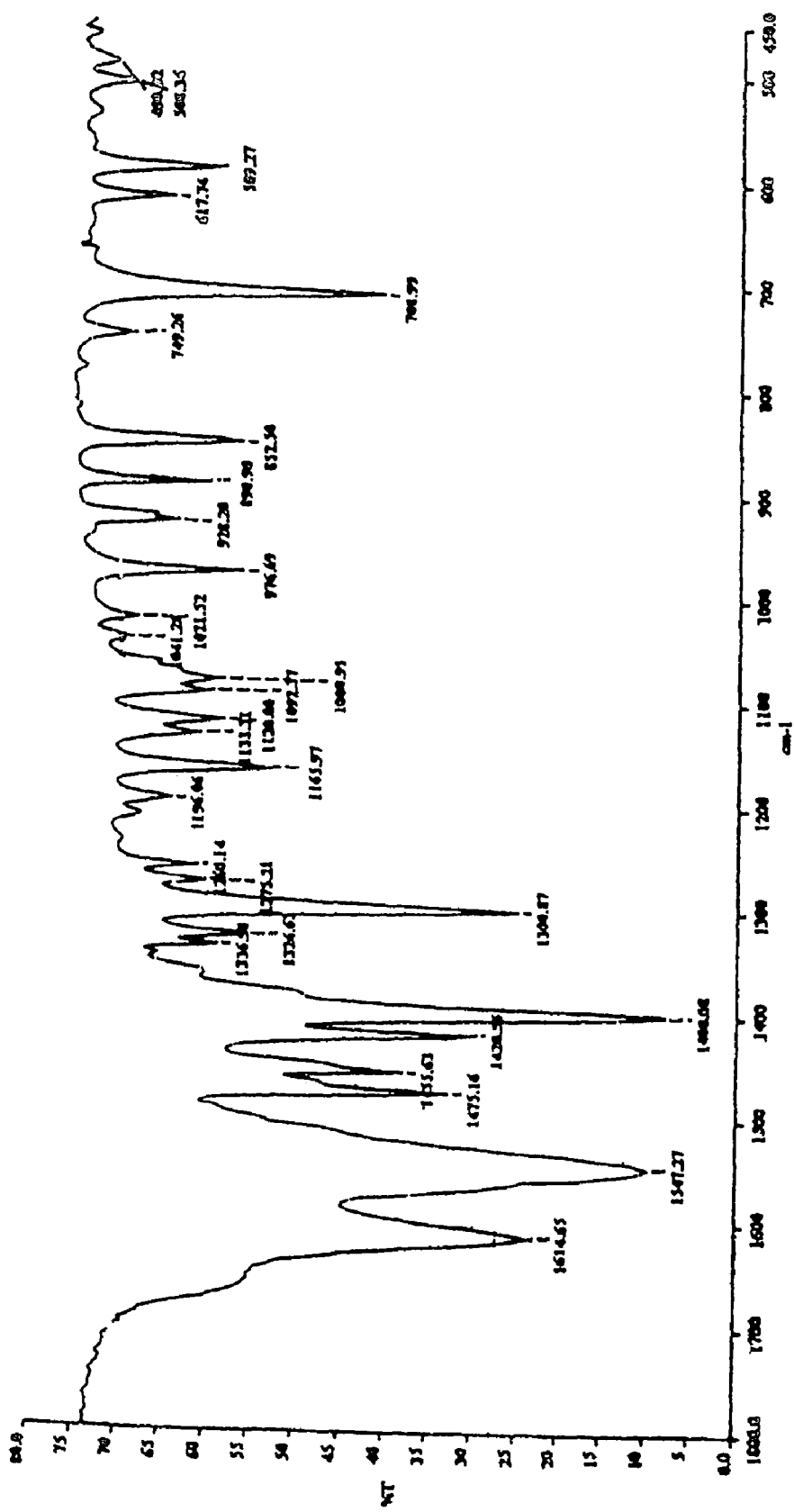
FIG. 4 is the FTIR spectrum of the Gabapentin Form-II
Figure 5:
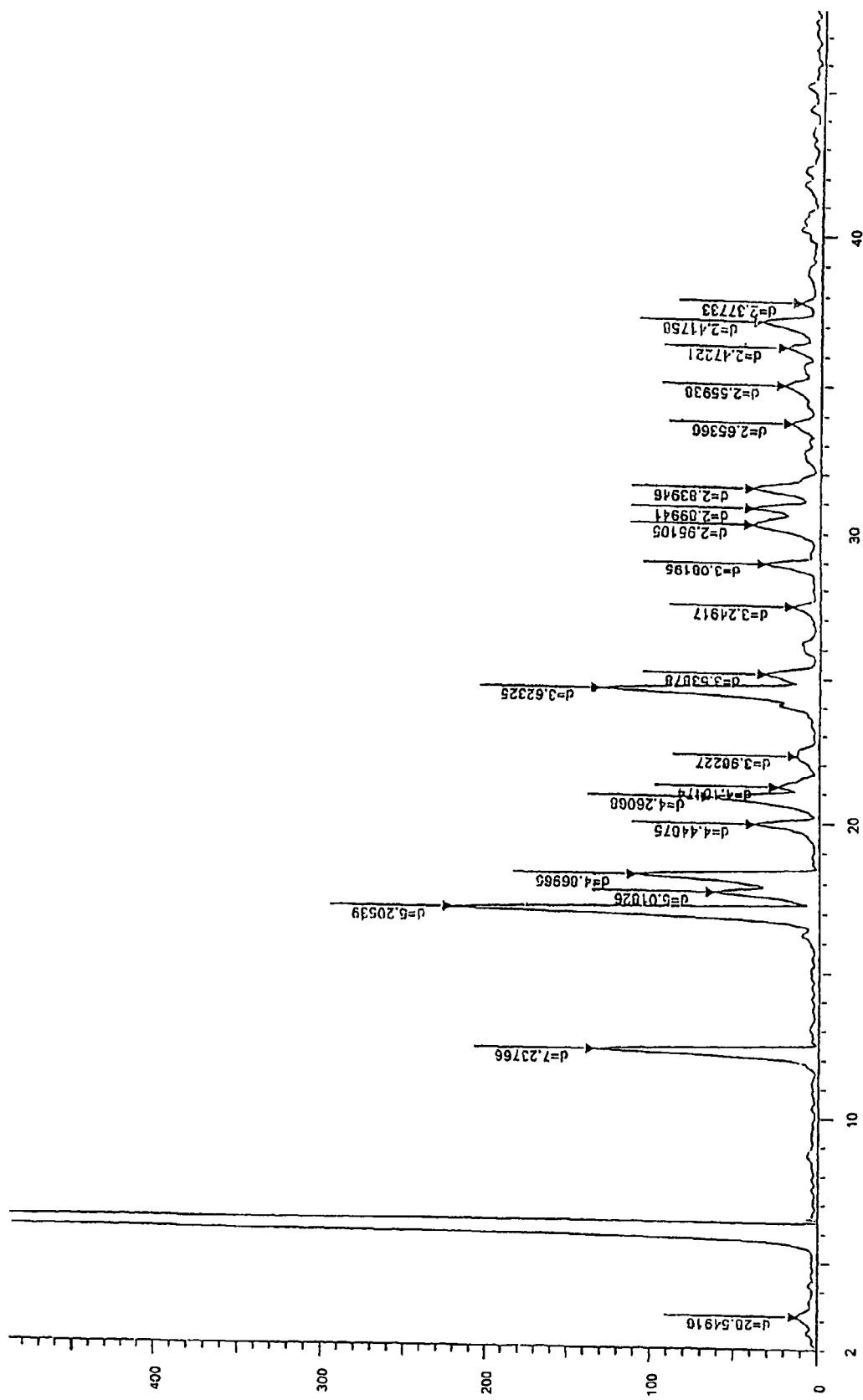
FIG. 5 is the X-ray diffraction pattern of the Gabapentin Form-III
Figure 6:
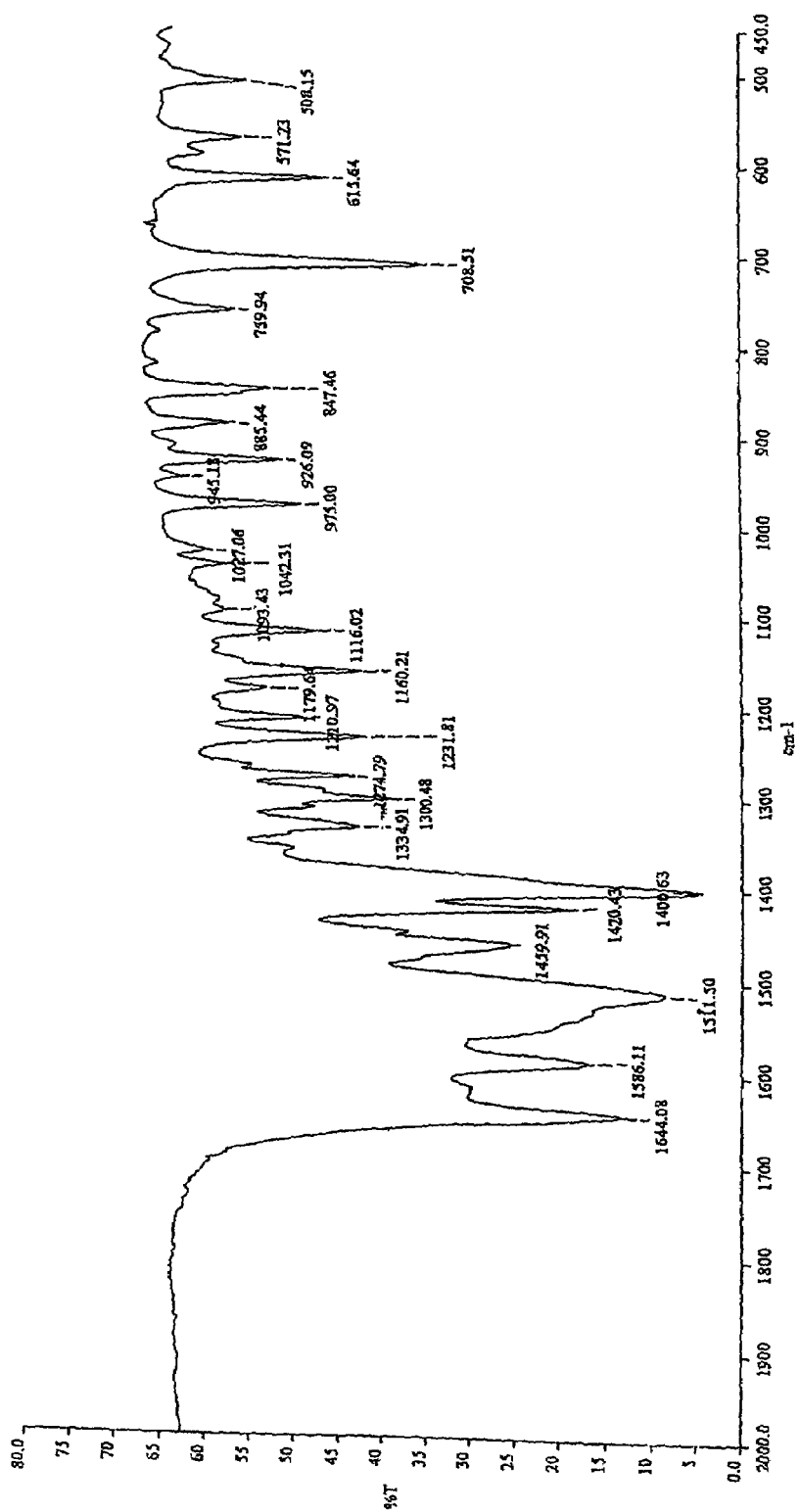
FIG. 6 is the FTIR spectrum of the Gabapentin Form-III
Figure 7:
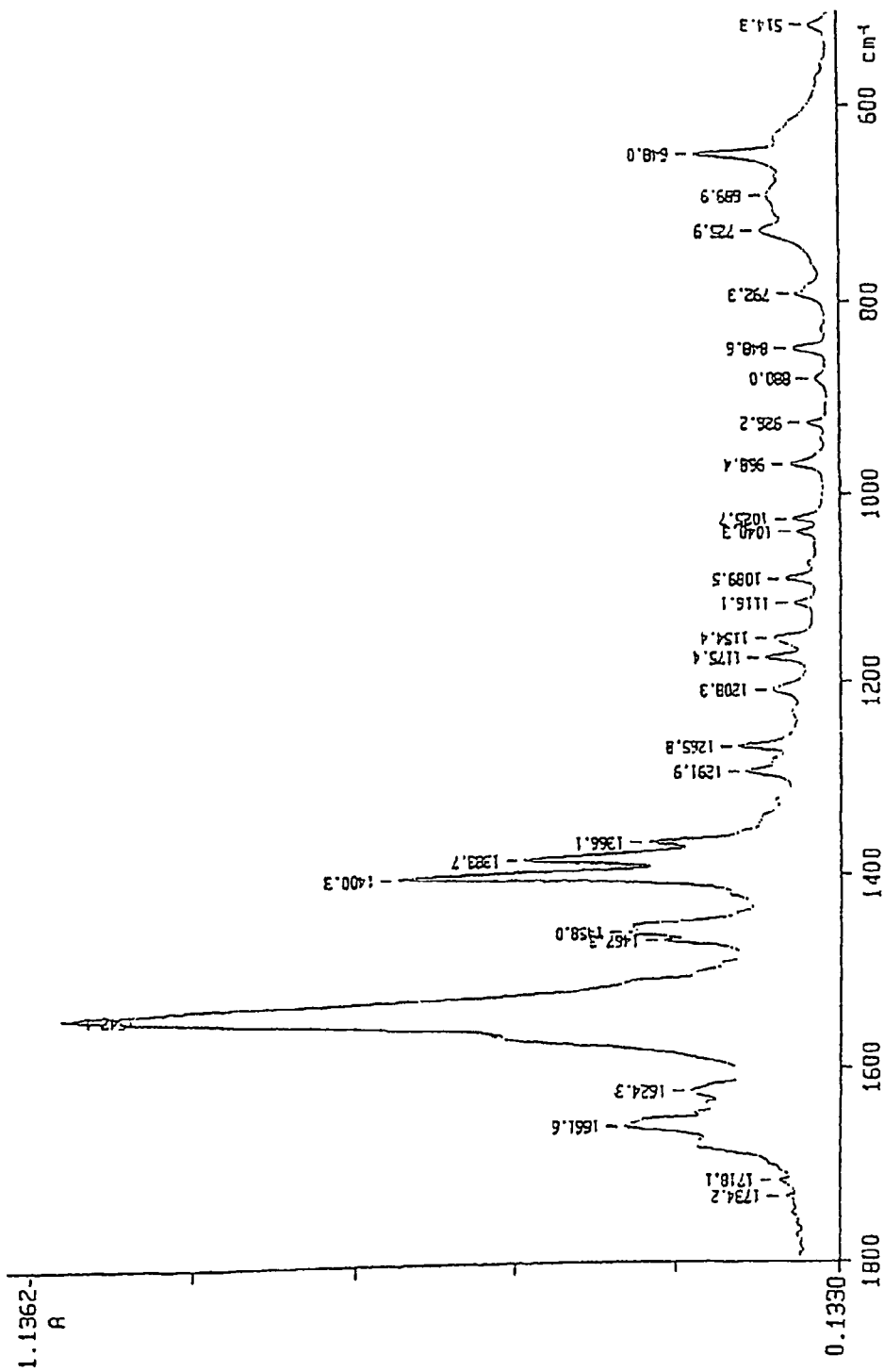
FIG. 7 is the FTIR spectrum of the Gabapentin hydrate

FTIR Peaks of Gabapentin hemisulphate hemihydrate, Form-II and Form-III

| S. No | Hemisulphate hemihydrate | Hydrate | Form-II | Form-III |
|---|---|---|---|---|
| 1 | 1714 | 1664 | | 1664 |
| 2 | 1627 | 1624 | 1615 | 1586 |
| 3 | 1581 | | 1546 | 1510 |
| 4 | 1525 | 1542 | 1476 | 1460 |
| 5 | 1461 | | 1420 | 1420 |

TABLE 1-continued

FTIR Peaks of Gabapentin hemisulphate hemihydrate, Form-II and Form-III

| S. No | Hemisulphate hemihydrate | Hydrate | Form-II | Form-III |
|---|---|---|---|---|
| 6 | 1430 | | 1400 | 1402 |
| 7 | 1392 | | 1337 | 1333 |
| 8 | 1315 | | 1327 | 1,311 |
| 9 | 1282 | 1292 | 1300 | 1290 |
| 10 | 1200 | 1175 | 1165 | 1180 |
| 11 | 1,146 | 1154 | 1,133 | 1160 |
| 12 | 1127 | 968 | 1120 | 1115 |
| 13 | 986 | | 976 | 974 |
| 14 | 941 | 926 | 928 | 945 |
| 15 | 917 | 880 | 922 | 926 |
| 16 | 901 | 726 | 890 | 885 |
| 17 | 757 | 648 | 749 | 760 |
| | 686 | | 709 | 708 |

XRD peaks and 2 theta values:

| S. No | Hemisulphate hemihydrate | Hydrate | Form-II | Form-III |
|---|---|---|---|---|
| 1 | 6.86 | 6.1 | 7.8 | 6.1 |
| 2 | 13.7 | 12.2 | 13.3 | 12.1 |
| 3 | 17.0 | 16 | 14.9 | 16.9 |
| 4 | 18.0 | 18.3 | 16.6 | 17.6 |
| 5 | 20.2 | 19.1 | 16.8 | 18.1 |
| 6 | 20.6 | 19.8 | 19.5 | 19.9 |
| 7 | 24.2 | 20.7 | 20.2 | 20.8 |
| 8 | 24.6 | 24.5 | 21.3 | 24.4 |
| 9 | 26.2 | 26.4 | 21.8 | 25.1 |
| 10 | 26.8 | 28.4 | 23 | 28.8 |
| 11 | 27.7 | 30.7 | 23.5 | 30.2 |
| 12 | 29.9 | 32.3 | 25.7 | 30.7 |
| 13 | 30.8 | | 26.9 | 31.5 |
| 14 | 34.0 | | 28 | |
| 15 | 34.7 | | | |

The essential features of the present invention consists of:
Reaction of 1,1-Cyclohexane diacetic acid mono amide with alkali hypo halite solution, acidification with sulphuric acid in presence of a solvent
Extraction of the formed sulphate salt into organic layer
Separation of the organic layer, drying over dehydrating agents
Addition of an ante solvent, cooling to precipitate the hemisulphate hemihydrate salt and its isolation
Dissolution of hemisulphate hemihydrate salt in a short chain alcohol,
Filtration of the solution to remove the insoluble materials
Neutralization of the filtrate with a base at specified temperature range to liberate the free amino acid
Separation of the liberated free amino acid by cooling, leaving the formed byproduct base-salt in the mother liquor/solvent,
Separation of the formed Gabapentin Form-II
Purification of the product by slurring in ethanol in a specified temperature range
Recovery of the product followed by drying The precipitated Gabapentin and the purified Gabapentin are identified by XRD and IR to be polymorphic Form-II.

The 1,1-cyclohexane diacetic acid mono amide used as starting material is prepared as per the literature (U.S. Pat. No. 4,024,175).

For the reaction of 1,1-cyclohexane diacetic acid mono amide with alkali hypo halite, the preferred alkali hypo halite Sodium hypo chlorite solution and the reaction is carried out in the temperature range of about −10° C. to about 5° C., with the preferred range between about −5° C. to about 5° C. Acidification of the reaction mass to a pH of about 2.0 and preferably below 2.0 in the range of about 1.0 to about 1.5 is carried out with sulphuric acid in presence of an organic solvent in a temperature range of about 15° C. to about 25° C. The preferred solvent is n-Butanol.

The reaction mass is allowed to settle and the organic layer is separated. The aqueous layer is extracted a few times with the solvent. The combined extracts is dried over dehydrating agents selected from materials such as anhydrous sodium sulphate, magnesium sulphate etc.

To the dried organic layer is treated with ante solvent, cooled if required to precipitate the hemisulphate hemihydrate salt. The ante solvent is selected from the hydrocarbons, aromatic hydrocarbons, alkyl ketones, alkyl ethers, the preferred solvent being hexane, toluene, acetone, di isopropyl ether or a their mixtures. The precipitated hemisulphate hemihydrate salt is separated by conventional methods such as filteration, centrifugation and dried to constant weight.

The Gabapentin hemisulphate hemihydrate salt is dissolved in short chain alcohols, preferred alcohol being Ethanol, n-Butanol at about 20° C. to about 25° C., filtered to remove the insolubles, and then raising the temperature of the filtrate to above 70° C. preferably from about 70° C. to about 75° C., slowly neutralized with organic base. The preferred bases are tri ethyl amine, di isopropyl ethyl amine, maintain the reaction mass for 1-2 hrs at the temperature above 60° C. in the preferable range of about 70° C to about 75° C., cooling the mass gradually to about 10° C. to 25° C., preferably to about 20° C. to about 25° C., stirring for about 1 to about 2 hrs followed by the separation of the precipitated free amino, washing of the wet cake with solvent such as ethanol and drying the product at temperature preferably between 45° C. to about 50° C.

The free amino acid is further purified by suspending in ethanol, raising the temperature to about 60° C. to about 65° C., maintaining the suspension at this temperature for about one hour followed by gradual cooling and stirring for about 1-2 hrs at temperature 20° C.-25° C. The purified product so formed is isolated and dried to obtain Gabapentin with chloride ions in the pharmaceutically acceptable range of 20-100 ppm and lactam impurity below 0.1%.

The invention can be further illustrated by a few non-limiting examples.

EXAMPLE-I

Stage-1: Preparation of Gabapentin Hemisulphate Hemihydrate

Sodium hypochlorite solution (6.25%, 625 g) is cooled to 10° C. and sodium hydroxide flakes (51 g) is dissolved in it by stirring for 10-15 min. at 10° C.-15° C. The mass is further cooled to −5° C. In a separate flask 1,1-cyclohexane diacetic acid monoamide (100 g) is dissolved in 4N Sodium hydroxide solution (150 ml) at 15° C.-20° C. The amide solution is slowly added to sodium hypochlorite solution at temperature −5° C. to −3° C. over 3 hrs. And then maintained at about 0° C. for 2 hrs. The temperature is then slowly raised to 20° C.-25° C. over 3 hrs and maintained for 4 hrs at 20° C.-25° C. Sodium metabisulphite solution (5 g in 10 ml water) is then added. The reaction mass is filtered to remove any undissolved material. pH of the filtrate is adjusted to 9.0 by the addition of 1:1 dilute sulphuric acid at temperature 20° C.-25° C. n-Butanol (200 ml) is added and the pH is further adjusted to 1.5 with sulphuric acid. The reaction mass is stirred for 10-15 min. and then allowed to settle. The layers are separated. The aq. layer is extracted with n-Butanol (200 ml). The combined extract is dried over anhydrous sodium sulphate (15 g). Di isopropyl ether (1200 ml) is slowly added at room temperature over 30-45 min to the dried extracted layer. The reaction mass is stirred for 1 hr and then cooled to 5° C. and stirred for 1 hr at about 0° C.-5° C. The product is filtered, washed with di isopropyl ether (50 ml) and dried at 45° C.-50° C. to constant weight.

The yield of dry wt of Gabapentin hemisulphate hemihydrate is 85 g (Yield: 73.8%). The XRD and IR spectra are given in table-1

Stage-2: Conversion of Gabapentin Hemisulphate Hemihydrate to Gabapentin Form-II The Gabapentin hemisulphate hemihydrate salt (100 g) prepared as above in stage-1 is suspended in ethanol (700 ml) and stirred for 30 min. at room temperature. The insolubles are filtered and washed with ethanol (50 ml). The filtrate is heated to 70° C.-75° C. and the pH of the filtrate is adjusted to 7.1-7.2 by slow addition of diisopropyl ethylamine solution (106 g in 145 ml ethanol) at 70° C.-75° C. over 60 min. The reaction mass is maintained for 2 hrs at 70° C.-75° C. and then gradually cooled to 20° C.-25° C. and maintained for about 1 hr. The filtered product is washed with ethanol (50 ml) and dried at 45° C.-50° C. to constant weight.

Dry wt of the Gabapentin Form-II is 50 g (Yield: 67%).

Stage-3: Purification of Gabapentin Form-II

Gabapentin Form-II (50 g) prepared as above is suspended in ethanol (300 ml) and the temperature is raised to 65° C. and maintained for 30 min. between 65° C.-70° C. The mass is cooled to room temperature and stirred for 30 min. at room temperature. The filtered product is washed with ethanol (25 ml) and dried at 50° C.-55° C. to constant weight.

The dry weight of Gabapentin Form-II is 45 g (Yield: 90%)

The XRD and IR of this product matched with the standard available for the Form-II

EXAMPLE-II

Stage-1: Preparation of Gabapentin Hemisulphate Hemihydrate

Sodium hypochlorite solution (6.25%, 625 g) is cooled to 10° C. and sodium hydroxide flakes (51 g) is dissolved in the hypochlorite solution by stirring for 10-15 min. at 10° C.-15° C. and further cooled to –5° C. In a separate flask 1,1-cyclohexane diacetic acid monoamide (100 g) is dissolved in 4N Sodium hydroxide solution (150 ml) at 15° C.-20° C. The amide solution is slowly added to sodium hypochlorite solution at temperature –5° C. to –3° C. over 3 hrs. The reaction mass is maintained for 2 hrs at about 0° C. and then the temperature is slowly raised to 20° C.-25° C. over 3 hrs and maintained for 4 hrs at 20° C.-25° C. Sodium metabisulphite solution (5.0 g in 10 ml water) is then added. The reaction mass filtered to remove any undissolved material. pH of the filtrate is adjusted to 9.0 by the addition of 1:1 dil sulphuric acid at temperature 20° C.-25° C. n-Butanol (200 ml) is added and the pH is further adjusted to 1.5 with sulphuric acid. The mass is stirred for 10-15 min., allowed to settle and the layers are separated. The aq. layer is extracted with n-Butanol (200 ml). The combined extracts are dried over anhydrous sodium sulphate (15 g). Acetone (1800 ml) is slowly added to the dried extracted layer at room temperature over 30-45 min. The system is then maintained for about 1 hr under stirring, cooled to 5° C. and stirred further for 1 hr at 0° C.-5° C. The filtered product is washed with acetone (50 ml) and dried at 45° C.-50° C. to constants weight.

The dry wt of the Gabapentin hemisulphate hemihydrate is 82 g (Yield: 71.4%),

Which was converted to Gabapentin Form-II by following the similar procedure as mentioned in Example-I, Stage-2 and Stage-3.

The XRD and IR spectra are given in table 1

The XRD and IR of this product matched with the standard available for the Form-II

The invention claimed is:

1. A process for the preparation of Gabapentin Form-II comprising the steps of:
    reacting 1,1-cyclohexane di acetic acid mono amide with an alkali hypo halite solution at a temperature of about –10° C. to about 5° C., followed by acidification with sulphuric acid in presence of a first organic solvent;
    extracting the formed sulphate salt into an organic layer with a second organic solvent;
    separating the organic layer, followed by drying the layer over dehydrating agents;
    adding an ante solvent to precipitate the formed hemisulphate hemihydrate salt followed by its isolation;
    dissolving the hemisulphate hemihydrate salt in a short chain alcohol and
    separating any insolubles from the salt solution to form a salt solution filtrate;
    neutralizing the filtrate with a base at temperature of about 70° C. to liberate free amino acid;
    isolating the liberated free amino acid by cooling, leaving formed byproduct base-salt in the mother liquor/solvent;
    separating the formed Gabapentin Form-II followed by purification by slurrying in ethanol at temperature of about 60° C.-70° C.; and
    recovering the final product by filtering and drying to obtain Gabapentin Form-II having sulphate ions less than 100 ppm with respect to Gabapentin.

2. A process as claimed in claim 1, wherein the first organic solvent is selected from n-Butanol, MIBIC, methyl ethyl ketone and THF.

3. A process as claimed in claim 1, wherein the second organic solvent is selected from n-Butanol, MIBK, THF and methyl ethyl ketone.

4. A process as claimed in claim 1, wherein drying of the organic layer is carried out over dehydrating agents.

5. A process as claimed in claim 1, wherein the ante solvent is selected from acetone, toluene, n-hexane, and di isopropyl ether.

6. A process as claimed in claim 1, wherein the short chain alcohol is ethanol and n-Butanol.

7. A process as claimed in claim 1, wherein the base is selected from di isopropyl ethylamine, and triethylamine.

8. A process as claimed in claim 1, wherein the neutralization temperature is in the range of 65°C.-75° C.

9. A process as claimed in claim 1, wherein the purification of Gabapentin is done by slurrying in ethanol in the temperature range 65°C.-70° C.

10. Crystalline Gabapentin hemisulphate hemihydrate characterized by powder x-ray diffraction peaks at 2-theta 6.8, 13.7, 17,0, 18.0, 20.2, 20.6, 24,2, 24.6, 26.2, 26.8, 27.7, 29.9, 30,8, 34.0, and 34.7 degrees.

11. Crystalline Gabapentin hemisulphate hemihydrate characterized by infra-red absorptions having peaks at 686, 757, 901, 917, 986, 1127, 1142, 1200, 1282, 1315, 1430, 1462, 1525, 1580 and 1714 $cm^{-1}$.

12. A process for the preparation of Gabapentin hemisulphate hemihydrate comprising the steps of:

reacting 1,1-cyclohexane di acetic acid mono amide with an alkali hypo halite solution at temperature of about −10° C. to about 5° C., followed by acidification with sulphuric acid in presence of a first organic solvent;

extracting the formed sulphate salt into an organic layer with a second organic solvent;

separating the organic layer, and drying it over dehydrating agents;

adding an ante solvent to the organic layer to precipitate a hemisulphate hemihydrate salt followed by its isolation; and isolating and drying Gabapentin hemisulphate hemihydrate.

13. A process as claimed in claim 12, wherein the first organic solvent is selected from n-Butane, MIBK, methyl ethyl ketone and THF.

14. A process as claimed in claim 12, wherein the second organic solvent is selected from n-Butanol, MIBK, THF and methyl ethyl ketone.

15. A process as claimed in claim 12, wherein the drying of the organic layer is carried out over dehydrating agents.

16. A process as claimed in claim 12, wherein the ante solvent is selected from acetone, toluene, n-hexane, and di isopropyl ether.

17. A process as claimed in claim 12, wherein the drying of the Gabapentin hemisulphate hemihydrate is at a temperature range of 50-60° C.

* * * * *